(12) United States Patent
Zhou

(10) Patent No.: US 7,226,907 B1
(45) Date of Patent: Jun. 5, 2007

(54) CARDIAC MUSCLE FUNCTION AND MANIPULATION

(75) Inventor: Mingdong Zhou, La Jolla, CA (US)

(73) Assignee: Zensun (Shanghai) Science & Technology Limited, Shanghai (CN)

(*) Notice: Subject to any disclaimer, the term of this patent is extended or adjusted under 35 U.S.C. 154(b) by 0 days.

(21) Appl. No.: 09/980,672

(22) PCT Filed: Dec. 21, 1999

(86) PCT No.: PCT/AU99/01137

§ 371 (c)(1),
(2), (4) Date: Mar. 8, 2002

(87) PCT Pub. No.: WO00/37095

PCT Pub. Date: Jun. 29, 2000

(30) Foreign Application Priority Data

Dec. 21, 1998 (AU) .................................. PP7850

(51) Int. Cl.
*A61K 38/00* (2006.01)
(52) U.S. Cl. ........................................................ 514/12
(58) Field of Classification Search ................ 514/2, 514/12
See application file for complete search history.

(56) References Cited

U.S. PATENT DOCUMENTS

| | | | |
|---|---|---|---|
| 3,773,919 A | 11/1973 | Boswell et al. ............... 424/19 |
| 4,179,337 A | 12/1979 | Davis et al. ................. 435/181 |
| 4,301,144 A | 11/1981 | Iwashita et al. .............. 424/78 |
| 4,485,045 A | 11/1984 | Regen ......................... 260/403 |
| 4,496,689 A | 1/1985 | Mitra ......................... 525/54.1 |
| 4,544,545 A | 10/1985 | Ryan et al. ................... 424/1.1 |
| 4,640,835 A | 2/1987 | Shimizu et al. ............... 424/94 |
| 4,670,417 A | 6/1987 | Iwasaki et al. ................ 514/6 |
| 4,791,192 A | 12/1988 | Nakagawa et al. .......... 530/399 |
| 5,367,060 A | 11/1994 | Vandlen et al. |
| 5,530,109 A | 6/1996 | Goodearl et al. |
| 5,641,869 A | 6/1997 | Vandlen et al. |
| 5,667,780 A | 9/1997 | Ho |
| 5,714,385 A | 2/1998 | Mather et al. |
| 5,716,930 A | 2/1998 | Goodearl et al. |
| 5,721,139 A | 2/1998 | Mather et al. |
| 5,834,229 A | 11/1998 | Vandlen et al. |
| 5,840,525 A | 11/1998 | Vandlen et al. |
| 5,856,110 A | 1/1999 | Vandlen et al. |
| 5,859,206 A | 1/1999 | Vandlen et al. |
| 5,968,511 A | 10/1999 | Akita et al. |
| 6,033,660 A | 3/2000 | Mather et al. |
| 6,087,323 A * | 7/2000 | Gwynne et al. ................ 514/2 |
| 6,096,873 A | 8/2000 | Schaefer et al. |
| 6,121,415 A | 9/2000 | Godowski et al. |
| 6,136,558 A | 10/2000 | Ballinger et al. |
| 6,156,728 A | 12/2000 | Gao |
| 6,162,641 A * | 12/2000 | Goldman et al. ........... 435/325 |
| 6,169,070 B1 | 1/2001 | Chen et al. |
| 6,252,051 B1 | 6/2001 | Godowski et al. |
| 6,387,638 B1 | 5/2002 | Ballinger et al. |
| 6,399,746 B1 | 6/2002 | Vandlen et al. |
| 6,444,642 B1 * | 9/2002 | Sklar et al. ..................... 514/8 |
| 6,446,242 B1 * | 9/2002 | Lien et al. ...................... 716/6 |
| 6,593,290 B1 | 7/2003 | Gao |
| 6,635,249 B1 | 10/2003 | Marchionni et al. |
| 6,750,196 B1 * | 6/2004 | Reh et al. ....................... 514/2 |

FOREIGN PATENT DOCUMENTS

| | | |
|---|---|---|
| AU | 68278/94 | 11/1994 |
| DE | 3218121 | 5/1982 |
| EP | 102324 | 7/1983 |
| EP | 133988 | 8/1984 |
| EP | 52322 | 3/1985 |
| EP | 58481 | 10/1986 |
| EP | 88046 | 12/1987 |
| EP | 143949 | 10/1988 |
| EP | 36676 | 9/1990 |
| EP | 142641 | 1/1991 |
| EP | 647449 | 6/1994 |
| JP | 83-118008 | 6/1983 |
| WO | WO 89/01489 A | 2/1989 |
| WO | WO 92/18627 | 10/1992 |
| WO | WO 94/00140 | 1/1994 |
| WO | 26298 * | 5/1994 ..................... 37/10 |
| WO | WO 94/26298 * | 5/1994 ..................... 37/10 |

(Continued)

OTHER PUBLICATIONS

Balligand et al. Cardiac endothelium and tissue growth. Progress in Cardiovascular Diseases (Jan./Feb. 1997),; 3(4):351-360.*

(Continued)

*Primary Examiner*—Christopher R. Tate
*Assistant Examiner*—Maury Audet
(74) *Attorney, Agent, or Firm*—Jones Day

(57) ABSTRACT

A method of causing cardiomyocyte growth and/or differentiation, the method comprising exposing a cardiomyocyte to neuregulin (NRG) thereby activating the MAP kinase pathway in the cardiomyocyte and causing growth and/or differentiation of the cardiomyocyte. Use of neuregulin, neuregulin polypeptide, neuregulin derivatives, or compounds which mimic the activities of neuregulins in the treatment or management of heart disease and heart failure in a mammal.

28 Claims, 6 Drawing Sheets

FOREIGN PATENT DOCUMENTS

| | | | |
|---|---|---|---|
| WO | WO 94/26298 | | 11/1994 |
| WO | WO 95/32724 | | 12/1995 |
| WO | WO 96/15812 | | 5/1996 |
| WO | WO 96/15812 A | | 5/1996 |
| WO | WO 97/09425 | | 3/1997 |
| WO | 18976 | * | 4/1999 |
| WO | WO 99/18976 | | 4/1999 |

OTHER PUBLICATIONS

Balligand et al."Cardiac Endothelium and Tissue Growth" Progress in Cardiovascular Diseases (1997) 39(4):351-360.

Chien et al. "Regulation of Cardiac Gene Expression During Myocardial Growth and Hypertrophy: Molecular Studies of an Adaptive Physiologic Response" FASEB Journal (1991) 5:3037-3046.

Colucci et al. "Pathphysiology of Heart Failure" Chapter 13 *In Heart Disease: A Textbook of Cardiovascular Medicine* Braunwald, ed. Saunders, Philadelphia. (1996) 5:394-420.

Dias et al. "The Molecular Basis of Skeletal Muscle Differentiation" Seminars in Diagnostic Pathology (1994) 11(1):3-14.

Epstein et al "Biological Activity of Liposome-Encapsulated Murine Interferon γ is Mediated by a Cell Membrane Receptor" Proc. Natl. Acad. Sci. USA (1985) 82:3688-3692.

Florini-Jr. et al. "Stimulation of Myogenic Differentiation by a Neuregulin, Glial Growth Factor 2" Journal of Biological Chemistry 271(22):12699-12702 (1996).

Hwang et al. "Hepatic Uptake and Degradation of Unilamellar Sphingomyelin/Cholesterol Liposomes: A Kinetic Study" Proc. Natl. Acad. Sci. USA (1980) 77:4030-4034.

Langer et al. "Biocompatibility of Polymeric Delivery Systems for Macromolecules" Journal of Biomedical Materials Research (1981) 15:267-277.

Parker et al. "p53-Independent Expression of $p21^{Cip1}$ in Muscle and Other Terminally Differentiating Cells" Science (1995) 267:1024-1027.

*Physicians Desk Reference.* (1994) Medical Economics Data Production Co., Montvale, NJ. pp. 2314-2320.

Rumyantsev "Interrelations of the Proliferation and Differentiation Processes During Cardiac Myogenesis and Regeneration" International Review Cytology (1977) 51:187-273.

Sidman et al. "Controlled Release of Macromolecules and Pharmaceuticals from Synthetic Polypeptides Based on Glutamic Acid" Biopolymers (1983) 22:547-556.

Simpson et al. "Myocyte Hypertrophy in Neonatal Rat Heart Cultures and Its Regulation by Serum and by Catecholamines" Circulation Research (1982) 51(6):787-801.

Zhao et al. "Neuregulins Promote Survival and Growth of Cardiac Myocytes" The Journal of Biological Chemistry (1998) 273(17):10261-10269.

Zhao et al. "Selective Disruption of Neuregulin-1 Function in Vertebrate Embryos Using Ribozyme-tRNA Transgenes" Development 125:1899-1907 (1998).

Zhou et al. "Retinoid-Dependent Pathways Suppress Myocardial Cell Hypertrophy" Proc. Natl. Acad. Sci. USA (1995) 92:7391-7395.

Holmes, et al., "Identification of Heregulin, a Specific Activator of p185.sup.erbB2," Science 256:1205-1210 (1992).

* cited by examiner

CARDIAC MUSCLE FUNCTION AND MANIPULATION

TECHNICAL FIELD

This invention relates to polypeptides which affect myocardial cell differentiation and organisation of cardiac muscle contractile units, assay for identifying such polypeptides, and methods for improving cardiac function by the administration of such polypeptides to patients with heart disease.

BACKGROUND OF THE INVENTION

Heart failure affects 1.5% of populations, approximately three million Americans, developing at a rate of approximately 400,000 new cases per year in USA. Current therapy for heart failure is primarily directed to using angiotensin-converting enzyme (ACE) inhibitors and diuretics. ACE inhibitors appear to slow progress to end-stage heart failure; however, they are unable to relieve symptoms in more than 60% of heart failure patients and reduce mortality of heart failure only by approximately 15–20%. Heart transplantation is limited by the availability of donor hearts. With the exception of digoxin, the chronic administration of positive inotropic agents has not resulted in a useful drug without adverse side effects, including increased arrhythmias, or sudden death. These deficiencies in current therapy suggest the need for additional therapeutic approaches.

Growth of cardiac muscle cells switches from proliferation to hypertrophy during heart development. The former process is characterised by an increase in cardiac muscle cell number, and the latter by an increase in cell size without DNA synthesis or cell division. This switch is associated with terminal differentiation of cardiac muscle cells and occurs gradually during heart development, starting during the late embryonic stages and ending a few weeks after birth. During this period, gene expression, particularly that involving the cell cycle and signalling, is reprogrammed. For example, expression of a number of receptor protein tyrosine kinases and other cell cycle components decreases. Cell phenotype is also changed as cell-cell adhesions and contractile proteins are more organised in terminal differentiated myocardial cells.

Adult heart hypertrophy is an important adaptive physiological response to increased demands for cardiac work or after a variety of pathological stimuli that lead to cardiac injury. Normal hypertrophic cells have a large size with increased and well organised contractile units, as well as strong cell-cell adhesions. Although pathologically hypertrophic cells also have large size and accumulation of proteins, they often display disorganisation of contractile proteins (disarray of sarcomeric structures) and poor cell-cell adhesions (disarray of myofibers). Thus, in pathological hypertrophy, the increase in size and accumulation of contractile proteins are associated with disorganised assembly of sarcomeric structures and a lack of robust cell-cell interactions (Braunwald (1994) in Pathphysiology of Heart Failure. (Braunwald, ed.); Saunsers, Philadelphia; Vol. 14, pp 393–402).

The disarray of myofibers and sarcomeres are important features of cardiomyopathy. The former is a disorder of cell-cell association, and the latter is disorganisation of heart muscle contractile proteins. They are influenced by specific cell signals. Thus, a number of signals, like growth factors and hormones, alter cell adhesion and sarcomeric structure. Without these stimuli, cardiomyocytes display disarray of the cytoskeleton and sarcomeric structures, as well as disassociation of cell-cell interactions. As cardiac muscle cell differentiation is tightly associated with cardiac cell remodelling, adhesion and contractile protein organisations, factors that stimulate myocardial cell differentiation may be critical for enhancing the assembly of adult cardiac muscle cell sarcomeric structures.

Studies in an in vitro model system of cardiac muscle cell have led to the identification of a number of mechanical, hormonal, growth factor, and pathological stimuli which can activate several independent phenotype features of cardiac hypertrophy (Chien et al. (1991) FASEB J. 5:3037–3046; Zhou et al., (1995) PNAS. USA, 92:7391–7395). Currently, there are at least three signal transduction pathways, involving both ras-, rho- and $G_q$ protein-dependent downstream effectors implicated in the activation of features of the hypertrophic response in these in vitro model systems. While a great deal of progress has been made in uncovering the signalling pathways which activate the ventricular muscle cell hypertrophic response, relatively little is known about the mechanisms which specifically stimulate terminal differentiation of cardiac muscle cells and the terminal differentiation-associated assembly of contractile proteins. Compounds that could influence these processes may be form a major new class of therapeutics for the treatment of a variety of cardiac diseases.

Neuregulins, a family of EGF-like growth factors, activate ErbB receptor tyrosine kinases that belong to the EGF receptor superfamily, and are involved in an array of biological responses: stimulation of breast cancer cell differentiation and secretion of milk proteins; induction of neural crest cell differentiation to Schwann cells: stimulation of skeletal muscle cell synthesis of acetylcholine receptors; and, promotion of myocardial cell survival and DNA synthesis. In vivo studies of neuregulin gene-targeted homozygous mouse embryos with severe defects in ventricular trabeculae formation and dorsal root ganglia development indicate that neuregulin is essential for heart and neural development. However, information on how neuregulin controls cell differentiation and its downstream signalling pathways is limited.

Within the heart, neuregulin and ErbB receptors are respectively expressed in the endocardial lining and cardiac muscle cell layer in early stages of development. Since these two layers are widely separated, the neuregulin ligand must transverse the space between the two cell layers to activate their cognate ErbB receptors. Activation of these receptors in myocardial cells is necessary for promoting muscle cell growth or migration toward the endocardium, which results in the formation of finger-like structures (ventricular trabeculae) between these two layers. It is not clear previously if neuregulin stimulates myocardial cell differentiation.

The present inventor has now found that neuregulin and/or its cellular action may be suitable for use in detection, diagnosis and treatment of heart disease. Moreover, the inventor believes that potential beneficial effects of neuregulin and/or its cellular action may be specific for heart muscle cells and not necessarily applicable to skeletal or smooth muscle cells since 1) heart, skeletal and smooth muscle are both embryological and functionally distinct; 2) factors involved in skeletal muscle growth and differentiation, such as MyoD, play little or no role in cardiac muscle growth and differentiation; 3) inactivation of the genes for ErbB2 or 4 receptors or neuregulin produces major defects in cardiac but not skeletal or smooth muscle development, 4) as shown here, the growth factor, insulin like growth factor-I (IGF-I) causes embryonic myocyte proliferation but unlike neuregulin does not stimulate differentiation of these cells. By contrast, IGF-I but not neuregulin, has been shown to induce muscle hypertrophy.

SUMMARY OF THE INVENTION

The present invention is based in part on the discovery that neuregulin enhances cardiac muscle cell differentiation and organisation of sarcomeric and cytoskeleton structures, as well as cell-cell adhesion. Neuregulin, neuregulin polypeptide, neuregulin derivatives, or compounds which mimic the activities of neuregulins, fall within the scope of the methods of the present invention and are abbreviated hereinafter as NRG.

In a first aspect, the present invention consists in a method of causing cardiomyocyte growth and/or differentiation, the method comprising exposing the cardiomyocyte to NRG thereby activating the MAP kinase pathway in the cardiomyocyte and causing growth and/or differentiation of the cardiomyocyte.

In a second aspect, the present invention consists in a method of inducing remodelling of muscle cell sarcomeric and cytoskeleton structures, or cell-cell adhesions, the method comprising treating the cells with neuregulin thereby activating the MAP kinase pathway in the cells and causing remodelling of the cell structures or the cell-cell adhesions.

It will be appreciated that neuregulin may be provided directly to the cell or provided indirectly by causing neuregulin to be produced in cells by inducing expression of the gene(s) involved in neuregulin production. The production may be in the same cell to which the method is directed in an autocrine manner or by some other cell in a paracrine manner.

In a third aspect, the present invention consists in a method of identifying polypeptides or compounds which stimulate cardiac muscle cell differentiation, the method comprising contacting the cardiac muscle with a test polypeptide or compound in the presence of an inducer of cardiac muscle cell proliferation in the form of neuregulin, and measuring the development of cardiac muscle cell differentiation.

The differentiation of cardiac muscle cells is preferably measured in cells exposed to neuregulin or other test polypeptides, or to a mixture of neuregulin with a test polypeptide. Differentiation of cardiac muscle cell can be measured in a variety of ways, including by calculation of increases or decreases in DNA synthesis, analysis of the time-course of phosphorylation of MAP kinases in cardiac muscle cells, evaluation of the expression of cell cycle inhibitor, $p21^{CIP1}$, phenotypic organisation of contractile units, accumulation of contractile units, phenotypic alteration of cytoskeleton actin fibers, and the phenotype of cell-cell adhesions.

In one preferred embodiment of the method of identifying polypeptides or compounds which stimulate cardiac muscle cell differentiation, cells are incubated with different concentrations of various peptides or compounds and the effect of the test peptide or compound in different concentrations on cardiac muscle cell differentiation measured.

In another preferred embodiment of identifying polypeptides or compounds which induce cardiac muscle cell differentiation that dominates over that of the putative inducer of cardiac muscle cell proliferation, insulin-like growth factor-1 (IGF-1), cells are incubated with IGF-1, with and without the test polypeptide or compound, and the ability of the test polypeptide or compound to inhibit IGF-1-mediated cardiac muscle cell DNA synthesis, assembly of sarcomeric structures and cell-cell adhesions are measured.

In a further embodiment, the cells are incubated with phenylephrine (PE) with and without the test polypeptide or compound, and the ability of the test polypeptide or compound to augment PE-mediated cardiac muscle cell differentiation is determined. A test polypeptide which stimulates cardiac muscle cell differentiation may stimulate the assembly of sarcomeres and thus enhance heart function in a variety of ways, including by activating neuregulin-specific receptors, e.g., ErbB2, ERbB3 and ErbB4.

In a fourth aspect, the present invention consists in a method of identifying polypeptides or compounds which inhibit neuregulin stimulation of ventricular muscle cell differentiation, the method comprising contacting the ventricular muscle cell with the test polypeptide or compound in the presence neuregulin and measuring any inhibition of neuregulin stimulation of the ventricular muscle cell.

A compound may inhibit neuregulin stimulation of ventricular muscle cell differentiation by blocking, suppressing, reversing, or antagonising the action of neuregulin. In one embodiment, the measurement is by detecting DNA synthesis of ventricular muscle cells.

In a fifth aspect, the present invention consists in a therapeutic method of treating or preventing disassociation of cardiac muscle cell-cell adhesion and/or the disarray of sarcomeric structures in a mammal, the method comprising administering to the mammal a therapeutically effective amount of a neuregulin or its derivatives.

In one preferred embodiment, the therapeutic method is directed to treating heart failure resulting from disassociation of cardiac muscle cell-cell adhesion and/or the disarray of sarcomeric structures in the mammal.

In a sixth aspect, the present invention consists in a method of preventing or lowering the incidence of heart disease in a mammal, the method comprising preventing or lowering the interference or effects of polypeptides or compounds on the action of neuregulin and its receptors, ErbBs, that produces heart failure.

In another embodiment, a therapeutic agent which mimics the effects of neuregulin is used to treat or prevent PE, or IGF-1-mediated cardiac muscle cell dysfunction.

In an seventh aspect, the present invention consists in a method of determining predisposition to heart disease or heart failure in a subject, the method comprising testing cardiac or related cells of the subject for the ability to express and/or produce normal or adequate levels of neuregulin or its cognate ErbB receptors. The inability to express and/or produce normal or adequate levels of neuregulin being indicative of predisposition to heart disease or heart failure.

In a eighth aspect, the present invention consists in the use of neuregulin, neuregulin polypeptide, neuregulin derivatives, or compounds which mimic the activities of neuregulins in the treatment or management of heart disease and heart failure.

In a ninth aspect, the present invention consists in the use of neuregulin, neuregulin polypeptide, neuregulin derivatives, or compounds which mimic the activities of neuregulins in the manufacture of a medicament for the treatment or management of heart disease and heart failure.

By using primary cultured myocardial cells as a model system, the present inventor evaluated neuregulin signalling in cardiac myocyte differentiation, maturation and assembly or maintenance of sarcomeric and cytoskeleton structures. To assay the neuregulin effect on cell signalling, embryonic cardiac muscle cells were incubated with recombinantly purified human neuregulin ligand (rhNRGβ2). Neuregulin at $10^{-8}$M resulted in sustained activation of MAP kinases for at least 21 hours, whereas only transient activation was observed with a lower concentration ($10^{-10}$M) of rhNRGβ2. Expression of the Cdk inhibitor, $p21^{CIP1}$, was enhanced by the $10^{-8}$M, but not the $10^{-10}$M concentration of the ligand. The higher ligand concentration, concomitant with this increase in $p21^{CIP1}$ expression, resulted in a decrease in DNA synthesis, that was associated with terminal differentiation, whereas an increase in DNA synthesis and continued proliferation was observed with the lower dose. Furthermore, when neuregulin was mixed with IGF-1, rhNRGβ2 at either concentrations ($10^{-8}$M, or $10^{-10}$M) did not show a negative effect on the DNA synthesis and significantly blocked IGF-1-stimulated cardiomyocyte proliferation. To further evaluate the NRG-stimulated myocardial cell differentiation, sarcomeric and cytoskeleton structures of cultured neonatal rat cardiac muscle cells were examined by Phalloidin staining and immunofluorescent staining with anti-α-actinin antibody. rhNRGβ2 dramatically improved sarcomeric and cytoskeleton structures, as well as cell-cell adhesions. Such an effect was not found from the cells stimulated with either insulin IGF-1 or PE. When rhNRGβ2 was mixed with either IGF-1 or PE, rhNRGβ2 improved the cell structures. The $10^{-8}$M concentration of rhNRGβ2 showed maximal effect on improvements of sarcomeres and cell-cell adhesions. In addition, neuregulin overrode the negative regulation of MHC-α expression mediated by PE stimulation. These findings indicate that NRG function through two distinct pathways: one activated at lower ligand concentrations results in cardiomyocyte growth, whereas the other, activated with higher concentrations, is mediated by sustained activation of the MAP kinase pathway and results in terminal differentiation and maturation.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described with reference to the following examples and drawings.

MODES FOR CARRYING OUT THE INVENTION

Figure 1:
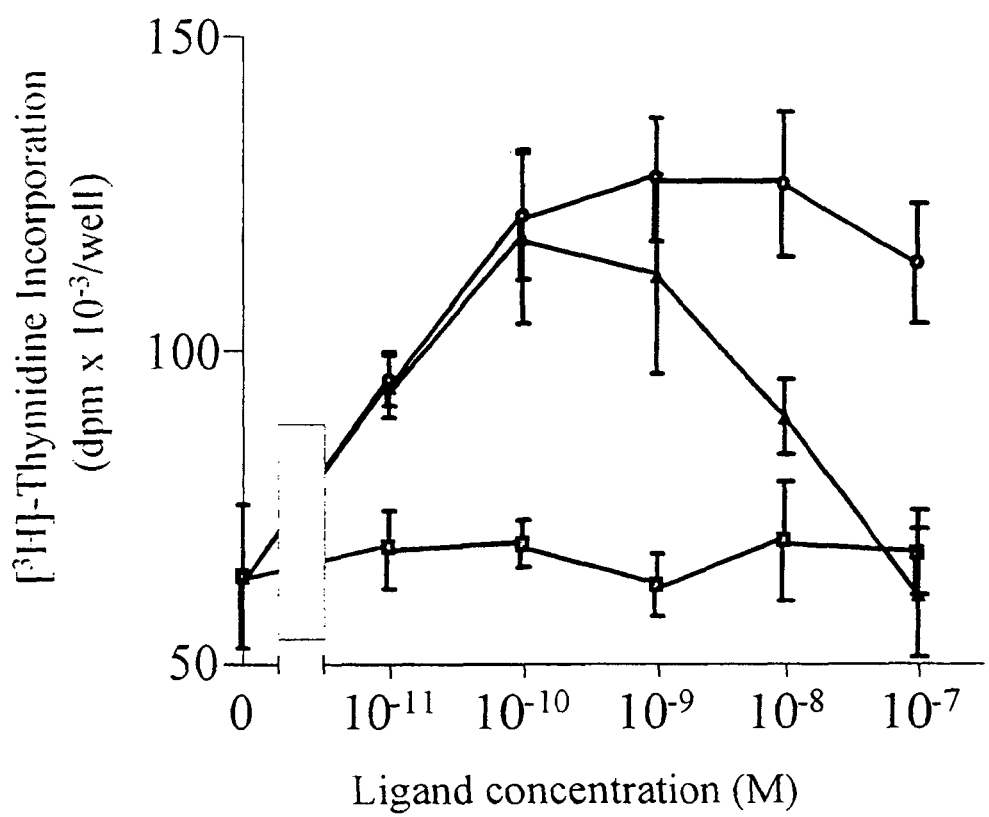
FIG. 1. Growth factor-stimulated DNA synthesis. DNA synthesis ([$^3$H] thymidine incorporation) by cultured embryonic mouse cardiomyocytes in response to 20 hr of treatment with the indicated concentrations of vehicle (purified Flag-peptide) (open square), recombinant human NRGβ2 (rhNRGβ2) (closed triangle) or insulin-like growth factor-I (IGF-I) (open circle). Data shown are the mean±S.E of five determinations with each treatment and at each concentration. All rhNRGβ2 reponses are significantly greater than control ($P<0.001$) except at $10^{-7}$M, and the rhNRGβ2 responses to concentration $^3$ $10^{-9}$M are significant than the respective IGF-I responses ($P<0.01$).

Utilising an in vitro system of cardiac muscle cell differentiation, a role for neuregulin in stimulating the activation of the differentiation response in comparison with two well-defined hormonal and growth factor stimuli, $\alpha_1$-adrenergic agonists and IGF-1 has been demonstrated. The present inventor has demonstrated that neuregulin differentiation pathways exist within cardiac muscle cells, and that neuregulin polypeptides can activate these pathways. Since cardiac muscle cell differentiation includes the processes of organisation of sarcomeric structures and cell-cell adhesions, the invention, thus, provides a useful method for the treatment and prevention of cardiac muscle cell with disorganisation of the sarcomeric structures and cell-cell adhesions, and the enhancement of heart function in cardiomyopathy, and for identifying polypeptides or compounds which activate cardiac muscle differentiation pathways.

Before the methods of the invention are described, it is to be understood that this invention is not limited to the particular methods described. The terminology used herein is for the purpose of describing particular embodiments only.

As used in this specification, the singular forms "a", "an", and "the" include plural references unless the context clearly dictates otherwise. Thus, for example, references to "neuregulin" or "a neuregulin peptide" includes mixtures of such neuregulins, neuregulin isoforms, and/or neuregulin-like polypeptides. Reference to "the formulation" or "the method" includes one or more formulations, methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference for the purpose of disclosing and describing material for which the reference was cited in connection with.

Definitions

"Neuregulin or neuregulin analogs" are molecules that can activate ErbB2/ErbB4 or ErbB2/ErbB3 heterodimer protein tyrosine kinases, such as all neuregulin isoforms, neuregulin EGF domain alone, neuregulin mutants, and any kind of neuregulin-like gene products that also activate the above receptors. The "neuregulin" used in this invention is the following polypeptide which is a fragment of human neuregulin β2 isoform containing the EGF-like domain, the receptor binding domain.

The cDNA sequence:

AGCCATCTTGTAAATGTGCGGAGAAGGAGAAAACTTTCTGTGTGAATGG

AGGGGAGTGCTTCATGGTGAAAGACCTTTCAAACCCCTCGAGATACTTGT

GAGGAGCTGTACCAG (SEQ ID NO:1)

The amino acid sequence encoded by the above DNA sequence:

SHLVKCAEKEKTFCVNGGECFMVKDLSNPSRYLCKCPNEFTGDRCQNYVM

ASFYKAEELYQ (SEQ ID NO:2).

"Cardiac muscle cell differentiation" is a condition characterised by the decrease in DNA synthesis by more than 10%, inhibition of other factor-stimulated DNA synthesis more than 10%, well organised sarcomeric structures and cell-cell adhesions, sustained activation of MAP kinases, and enhanced expression of $p21^{CIP1}$.

"Organised, or enhanced organisation of sarcomeres or sarcomeric structures" is a condition characterised by the straight array of contractile proteins revealed by immunofluorescent staining of α-actinin in cardiac muscle cells. The straight array of α-actinin proteins in cells can be distinguished by microscopy and its connected photography as exampled in Figures of this specification.

"Disorganised or disarray of sarcomeres or sarcomeric structures" is the opposite meaning of the above definitions.

"Organised, or enhanced organisation of cytoskeleton structures" is a condition characterised by the straight actin fibers revealed by phalloidin staining of cardiac muscle cells. The straight actin fibers in cells can be distinguished by microscopy and its connected photography as exampled in Figures of this specification.

"Disorganised or disarray of cytoskeleton structures" is the opposite meaning of the above definitions.

"Sustained activation of MAP kinases" is that phosphorylated state of MAP kinases, p42/44, is maintained for at least 21 hr in cells.

"Enhanced expression of $p21^{CIP1}$" is that expression of $p21^{CIP1}$ is increased at least 50% that is maintained for at least 24 hr in cells.

"The treatment of heart diseases" includes all suitable kinds of methods, such as vein injection of the neuregulin polypeptide, and gene therapy methods, in which heart or other cells were forced to contain a gene encoding neuregulin or derivatives for the treatment of heart diseases. For example, Adenovirus or Adeno-Associated-Virus can be used as a carrier to deliver neuregulin gene into infected heart or other cells. The infected cell can then express and secret neuregulin polypeptide to activate ErbBs on cardiac muscle cells.

"Ventricular muscle cell hypertrophy" is a condition characterised by an increase in the size of individual ventricular muscle cells, the increase in cell size being sufficient to result in a clinical diagnosis of the patient or sufficient as to allow the cells to be determined as larger (e.g., 2-fold or more larger than non-hypertrophic cells). It may be accompanied by accumulation of contractile proteins within the individual cardiac cells and activation of embryonic gene expression.

In vitro and in vivo methods for determining the presence of ventricular muscle cell hypertrophy are known. In vitro assays for ventricular muscle cell hypertrophy include those methods described herein, e.g., increased cell size and increased expression of atrial natriuretic factor (AND). Changes in cell size are used in a scoring system to determine the extent of hypertrophy. These changes can be viewed with an inverted phase microscope, and the degree of hypertrophy scored with an arbitrary scale of 7 to 0, with 7 being fully hypertrophied cells, and 3 being non-stimulated cells. The 3 and 7 states may be seen in Simpson et al. (1982) Circulation Res. 51: 787–801, FIG. 2, A and B, respectively. The correlation between hypertrophy score and cell surface area ($\mu m^2$) has been determined to be linear (correlation coefficient=0.99). In phenylephrine-induced hypertrophy, non-exposed (normal) cells have a hypertrophy score of 3 and a surface area/cell of 581 $\mu m^2$ and fully hypertrophied cells have a hypertrophy score of 7 and a surface area/cell of 1811 $\mu m^2$, or approximately 200% of normal. Cells with a hypertrophy score of 4 have a surface area/cell of 771 $\mu m^2$, or approximately 30% greater size than non-exposed cells; cells with a hypertrophy score of 5 have a surface area/cell of 1109 $\mu m^2$, or approximately 90% greater size than non-exposed cells; and cells with a hypertrophy score of 6 have a surface area/cell of 1366 $\mu m^2$, or approximately 135% greater size than non-exposed cells. The presence of ventricular muscle cell hypertrophy preferably includes cells exhibiting an increased size of about 15% (hypertrophy score 3.5) or more. Inducers of hypertrophy vary in their ability to induce a maximal hypertrophic response as scored by the above-described assay. For example, the maximal increase in cell size induced by endothelin is approximately a hypertrophy score of 5.

"Suppression" of ventricular muscle cell hypertrophy means a reduction in one of the parameters indicating hypertrophy relative to the hypertrophic condition, or a prevention of an increase in one of the parameters indicating hypertrophy relative to the normal conditions. For example, suppression of ventricular muscle cell hypertrophy can be measured as a reduction in cell size relative to the hypertrophic condition Suppression of ventricular muscle cell hypertrophy means a decrease of cell size of 10% or greater relative to that observed in the hypertrophic condition. More preferably, suppression of hypertrophy means a decrease in cell size of 30% or greater; most preferably, suppression of hypertrophy means a decrease of cell size of 50% or more. Relative to the hypertrophy score assay when phenylephrine is used as the inducing agent, these decreases would correlate with hypertrophy scores of about 6.5 or less, 5.0–5.5, and 4.0–5.0, respectively. When a different agent is used as the inducing agent, suppression is measure relative to the maximum cell size (or hypertrophic score) measured in the presence of that inducer.

Prevention of ventricular muscle cell hypertrophy is determined by preventing an increase in cell size relative to normal cells, in the presence of a concentration of inducer sufficient to fully induce hypertrophy. For example, prevention of hypertrophy means a cell size increase less than 200% greater than non-induced cells in the presence of maximally-stimulating concentration of inducer. More preferably, prevention of hypertrophy means a cell size increase less than 135% greater than non-induced cells; and most preferably, prevention of hypertrophy means a cell size increase less than 90% greater than non-induced cells. Relative to the hypertrophy score assay when phenylephrine is used as the inducing agent, prevention of hypertrophy in the presence of a maximally-stimulating concentration of phenylephrine means a hypertrophic score of about 6.0–6.5, 5.0–5.5, and 4.0–4.5, respectively.

In vivo determination of hypertrophy include measurement of cardiovascular parameters such as blood pressure, heart rate, systemic vascular resistance, contractility, force of heart beat, concentric or dilated hypertrophy, left ventricular systolic pressure, left ventricular mean pressure, left ventricular end-diastolic pressure, cardiac output, stroke index, histological parameters, and ventricular size and wall thickness. Animal models available for determination of development and suppression of ventricular muscle cell hypertrophy in vivo include the pressure-overload mouse model, RV murine dysfunctional model, transgenic mouse model, and post-myocardial infarction rat model. Medical methods for assessing the presence, development, and suppression of ventricular muscle cell hypertrophy in human patients are known, and include, for example, measurements of diastolic and systolic parameters, estimates of ventricular mass, and pulmonary vein flows.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

preventing the disease from occurring in a subject which may be predisposed to the disease but has not yet been diagnosed as having it;

inhibiting the disease. i.e., arresting its development; or relieving the disease, i.e., causing regression of the disease.

The invention is directed to treating patients with or at risk for development of heart disease and related conditions, e.g., heart failure. More specifically, "treatment" is intended to mean providing a therapeutically detectable and beneficial effect on a patient suffering from heart disease.

By the term "heart failure" is meant an abnormality of cardiac function where the heart does not pump blood at the rate needed for the requirements of metabolising tissues. Heart failure includes a wide range of disease states such as congestive heart failure, myocardial infarction, tachyarrythmia, familial hypertrophic cardiomyopathy, ischaemic heart disease, idiopathic dilated cardiomyopathy, and myocarditis. The heart failure can be caused by any number of factors, including ischaemic, congenital, rheumatic, or idiopathic forms. Chronic cardiac hypertrophy is a significantly diseased state which is a precursor to congestive heart failure and cardiac arrest.

"Treatment" refers to both therapeutic treatment and prophylactic or preventative measures, wherein the object is to prevent or slow down (lessen) hypertrophy. Those in need of treatment include those already with the disorder as well as those prone to have the disorder or those in which the disorder is to be prevented. The hypertrophy may be from any cause which is responsive to retinoic acid, including congenital, viral, idiopathic, cardiotrophic, or myotrophic causes, or as a result of ischaemia or ischaemic insults such as myocardial infarction. Typically, the treatment is performed to stop or slow the progression of hypertrophy, especially after heart damage, such as from ischaemia, has occurred. Preferably, for treatment of myocardial infarctions, the agent(s) is given immediately after the myocardial infarction, to prevent or lessen hypertrophy.

The terms "synergistic, "synergistic effect" and like are used herein to describe improved treatment effects obtained by combining one or more therapeutic agents with one or more retinoic acid compounds. Although a synergistic effect in some fields is meant an effect which is more than additive (e.g., 1+1=3), in the field of medical therapy an additive (1+1=2) or less than additive (1+1=1.6) effect may be synergistic. For example, if each of two drugs were to inhibit the development of ventricular muscle cell hypertrophy by 50% if given individually, it would not be expected that the two drugs would be combined to completely stop the development of ventricular muscle cell hypertrophy. In many instances, due to unacceptable side effects, the two drugs cannot be administered together. In other instances, the drugs counteract each other and slow the development of ventricular muscle cell hypertrophy by less than 50% when administered together. Thus, a synergistic effect is said to be obtained if the two drugs slow the development of ventricular muscle cell hypertrophy by more than 50% while not causing an unacceptable increase in adverse side effects.

Materials and Methods

Reagents and Antibodies

The following antibodies and reagents were used: IGF (Boehringer); collagenase (Worthington); pancreatin (Gibco BRL); MEK1 (MAPKK) inhibitor (PD98059) (New England); [methyl-$^3$H]thymidine (Amersham); monoclonal anti-erbB2 antibody (Novocastra); monoclonal IgG$_{2b}$ p21$^{CIP1}$ (F-5) (Santa Cruz); monoclonal anti-phospho-tyrosine horse radish peroxidase (HRPO)-conjugated antibody, RC20 (Transduction Laboratories); monoclonal anti-α-sacromeric actin antibody (clone 5c5), HRPO-conjugated anti-rabbit Ig, and anti-mouse Ig (Sigma); PhosphoPlus® p44/42 MAP kinase (Thr202/Tyr204) antibody kit (New England); anti-FLAG® M1 affinity gel and anti-FLAG M2monoclonal antibody (Eastman Kodak) mAb MF20 to sarcomeric myosin heavy chain (kindly provided by R. P. Harvey, Victor Chang Cardiac Research Institute); anti-sarcomeric α-actin antibody (Sigma).

Recombinant Human NRGβ2 Expression and Purification

A cDNA encoding the EGF-like domain of human NRGβ2 isoform (rhNRGβ2), residues 177–237, was inserted into the pFLAG1 expression vector (IBI) (a gift from Dr. Rodney J. Fiddes, Co-operative Research Centre for Biopharmaceutical Research, Australia). rhNRGβ2 with a FLAG-peptide attached at its N-terminus, was expressed in the periplasmic space of *E. coli* DH5α, and purified by affinity chromatography using anti-FLAG M1 monoclonal antibody according to the manufacturer's instructions. The purity of rhNRGβ2 was more than 90% as evidenced by SDS-PAGE separation and Coomassie Blue staining of purified protein samples. The concentration of purified proteins was determined using a Bio-Rad protein assay kit. Activity of the purified proteins was assayed by stimulation of MCF-7 breast cancer cell ErbB receptors with various ligand doses. This revealed increased ErbB receptor phosphorylation with increasing ligand concentration ($10^{-12}$M to $10^{-8}$M).

Primary Cultures of Mouse Cardiac Myocytes

Mouse embryos (E11.5–12.5) were used to prepare primary cardiac myocytes. Heart tissue was isolated aseptically from embryos. Myocardial cells were isolated by collagenase digestion and separated from non-cardiomyocytes by preattachments on culture dishes that was performed three times. Cells were then cultured as described previously. Using this method, it was routinely possible to obtained primary cultures with >90% myocytes.

ErbB and MAP Kinase Phosphorylation, and MAP Kinase Activity

Embryonic myocardial cells were cultured in serum-free medium for at least 24 hrs and then stimulated with rhNRGβ2 or IGF-I for various times. Stimulation was terminated by washing cells rapidly with cold PBS. To block the MAP kinase activation, the MEK inhibitor, PD98059, was added to the medium 30 mins prior to the adminstration of rhNRGβ2 or IGF-I. Cells were then harvested as previously described for Western blot analysis with HRPO-conjugated monoclonal antibody RC20H (1:2,000) for detection of phosphorylated ErbB receptors, or a phospho-specific p42/p44 MAP kinase antibody (dilution ratio 1:1,000) for detection of phosphorylated MAP kinases. The same amount of cell extract protein was loaded into each lane and separated by SDS-PAGE. Immunobloting with an anti-ErbB receptor or anti-p42/44 MAP kinase antibodies was also used to normalise for protein loading. MAP-kinase (p42/p44) activity was measured using a p42/44 MAP kinase enzyme assay kit (RPN84; Amersham, Bucks., U.K.) according to the manufacturer's instructions.

Detection of p21$^{CIP1}$ Protein

Embryonic myocardial cells cultured in serum-free or 5% FBS medium were stimulated with various concentrations of rhNRGβ2 with or without the MEK inhibitor, PD98059, for 24 or 48 hrs, harvested as described above and subjected to immunoblot analysis using an anti-p21$^{CIP1}$ antibody (1:100). The same amount of protein was loaded into each well of a SDS polyacrylamide gel. After immunobloting, the membrane was stripped and probed further with an antibody to the ErbB2 receptor for normalisation of protein loading.

Thymidine Incorporation

Embryonic myocardial cells were cultured with rhNRGβ2 or IGF-I containing serum-free DMEM for 20 hrs. [methyl-$^3$H] Thymidine (0.5 μCi/well) was added and cells were then cultured for a further 12 hrs. After rinsing twice with cold PBS, once with ice-cold 10% trichloroacetic acid, and then five times with ice-cold PBS, the cells were dissolved in 100 μl of 1% SDS, and counted in a liquid scintillation counter.

Immunofluorescent and Phalloidin Staining

Myocardial cells were plated in 2-well Novex plates (Nunc), and cultured with or without rhNRGβ2 in serum-free DMEM medium for 24–48 hour. After rinsing the cells with PBS, they were fixed with 4% paraformaldehyde and 0.1% Triton X-100 at room temperature for 30 minutes. The fixed cells were then blocked with 5% skim milk in PBS for 1 hr, followed by incubation with an anti-α-actinin monoclonal antibody (Sigma), for 45 minutes at room temperature. After washing, anti-mouse IgG conjugated with FITC (Sigma) was added and the cells were incubated for another half hour. For phalloidin staining, cells were fixed with 4% formadehyde for 1 hr., washed, and stained with phalloidin buffer (100 μl PBS, 10 ul rhodamine phalloidin (6.6 μM in MeOH)) for 1 hr. After PBS washing, cells were mounted with 1% p-phenylenediamine (1 mg/ml, Sigma) in glycerol, and then covered and sealed. Cells were examined using a UV fluorescent microscope and photographed with a 40x power objective.

All of the above assays were repeated at least three times for each experiments. Data for DNA synthesis and MAP kinase activity are presented as the mean±S.E of five replicate samples. Statistical significance was determined by ANOVA using the SAS statistical package with P<0.05 being considered significant. Immunoblots were quantitated by densitometry analysis with the intensity of the evaluated protein bands being shown below the blots as the fold changes over control (see Figures).

Results

NRG Regulates Embryonic Myocardial Cell DNA Synthesis

DNA synthesis in primary embryonic mouse cardiomyocytes (E11.5–12.5) was evaluated to investigate their growth response to NRG following stimulation with rhNRGβ2. As shown in FIG. 1, rhNRGβ2 at a concentration of $10^{-10}$M produced an approximately 2-fold increase in the DNA synthesis. However, DNA synthesis decreased with ligand concentrations>$10^{-10}$M. In contrast to the response to rhNRGβ2, myocardial cells showed only a proliferative response to recombinant human insulin-like growth factor I (IGF-I), in concentrations ranging from $10^{-11}$M to $10^{-7}$M. Inhibition of DNA synthesis by the higher concentrations of NRG was not due to E. coli proteins contaminating the bacterially-expressed rhNRGβ2, since proteins purified from bacteria transformed with FLAG-vector alone did not inhibit DNA synthesis. Moreover, to avoid possible effects of E. coli proteins, both commercially obtained IGF-I and purified rhNRGβ2 were disolved or diluted with anti-FLAG-protein preparations ($10^{-8}$M of FLAG peptide). These reagents showed identical activities to those prepared with PBS in stimulating myocardial cell DNA synthesis.

NRG Activates Embryonic Myocardial Cell ErbB Receptors

Figure 2A:
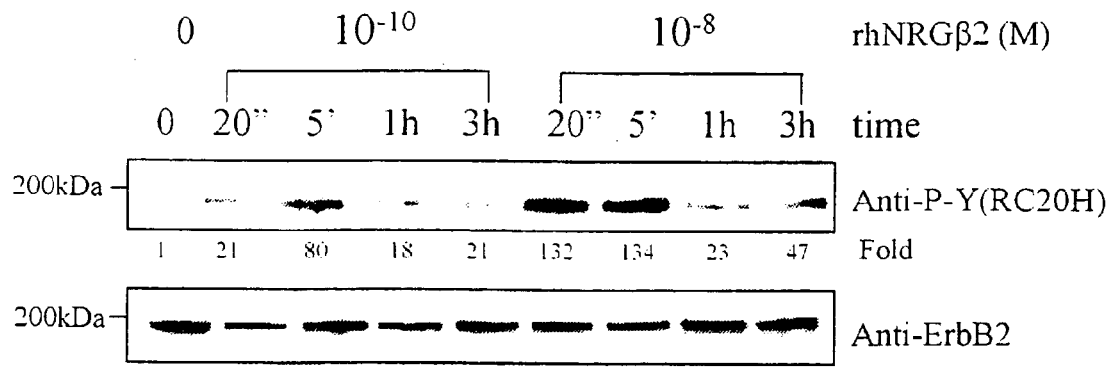
FIG. 2. NRG-mediated ErbB receptor phosphorylation. (a) Serum-starved cardiomyocytes were stimulated with vehicle (0) or rhNRGβ2 at a concentration of either $10^{-10}$M or $10^{-8}$M for the times indicated. Phosphorylation of ErbB receptors was then determined as described in Methods using an anti-phosphotyrosine antibody (RC20H). Fold increases in immunoblot intensities are shown, which were normalised for protein load based on the intensities of simultaneously determined immunoblots of ErbB2 shown below the phosphotyrosine species. (b) Phosphorylation of immunoprecipitated ErbB2 (top panel) or ErbB4 (bottom panel) resulting from the stimulation of embryonic cardiomyocytes for 5 min with $10^{-10}$M or $10^{-8}$M rhNRGβ2. Studies were performed as detailed in Methods and the immunoprecipitated products evaluated by immuno-blotting with anti-phosphotyrosine, anti-ErbB2 or anti-ErbB4 antibodies. Fold changes in immunoblot intensities are shown, which were normalised for protein loading based on the intensities of simultaneously determined immunoblots of ErbB2 or ErbB4 shown below the phosphotyrosine species.
Figure 2B:
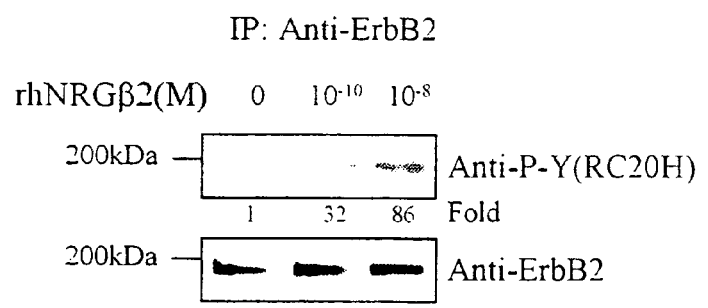
Figure 2B:
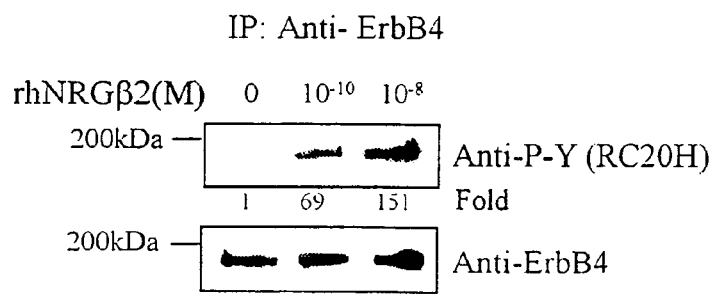

Of the four members of the ErbB receptor family (ErbB1–4), ErbB2 and ErbB4 are most abundantly expressed in cardiac myocytes. Phosphorylation of ErbB2 and ErbB4 receptors was evaluated by Western blot analysis of cell lysates, following stimulation with either $10^{-8}$M or $10^{-10}$M rhNRGβ2. As shown in FIG. 2a, a higher level of phosphorylated 180–185 kDa proteins corresponding to ErbB2/ErbB4 receptors, was evident with the higher concentration of NRG. The levels of phosphorylation gradually decreased with time. The concentration dependence of p180–185 protein phosphorylation corresponded to that for the decrease in DNA synthesis with rhNRGβ2 treatment (FIG. 1). ErbB2 and ErbB4 receptors were also immunoprecipitated using anti-ErbB2 or ErbB4 antibodies, and examined by Western blotting with anti-phospho-tyrosine antibodies. As shown in FIG. 2b, phosphorylation of both receptors was dependent on rhNRGβ2 concentrations. Although ErbB2 and ErbB4 phosphorylation levels differed slightly between experiments, the relative phosphorylation difference between high and low concentrations of rhNRGβ2 persisted.

NRG Concentration-Dependent Activation of MAP Kinases

Figure 3A:
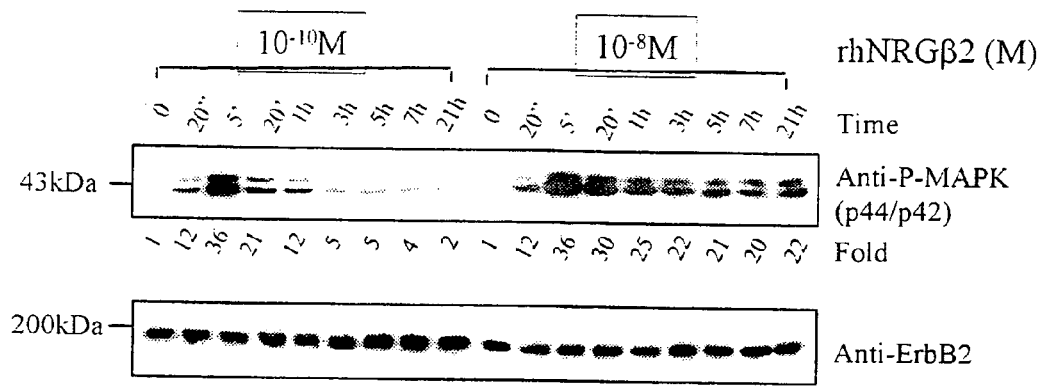
FIG. 3. NRG or IGF-I stimulated MAP kinase activation. (a) MAP kinase phosphorylation resulting from embryonic cardiomyocyte stimulation with rhNRGβ2 ($10^{-10}$M or $10^{-8}$M) for the times shown. After treatment with rhNRGβ2, cell extracts were prepared and evaluated for MAP kinase phosphorylation using an anti-phospho MAP kinase antibody, as described in Methods. Fold changes in immunoblot intensities are shown below the phosphotyrosine species. To control for protein loading, cell extracts were simultaneously evaluated for ErbB2 expression by immunoblot analysis using an anti-ErbB2 antibody. (b) MAP kinases catalytic activity was determined as described in Methods using extracts prepared from cardiomyocytes treated with rhNRGβ2 ($10^{-10}$M or $10^{-8}$M) for the times indicated, and shown as fold increase over the basal level activity of cells which were not stimulated with rhNRGβ2. Values of the fold shown as the means±SE of five determinations with each treatment and at each concentration. (c) MAP kinase phosphorylation resulting from IGF-I ($10^{-9}$M) stimulation of embryonic cardiomyocytes for the times indicated, was determined as in (a).
Figure 3B:
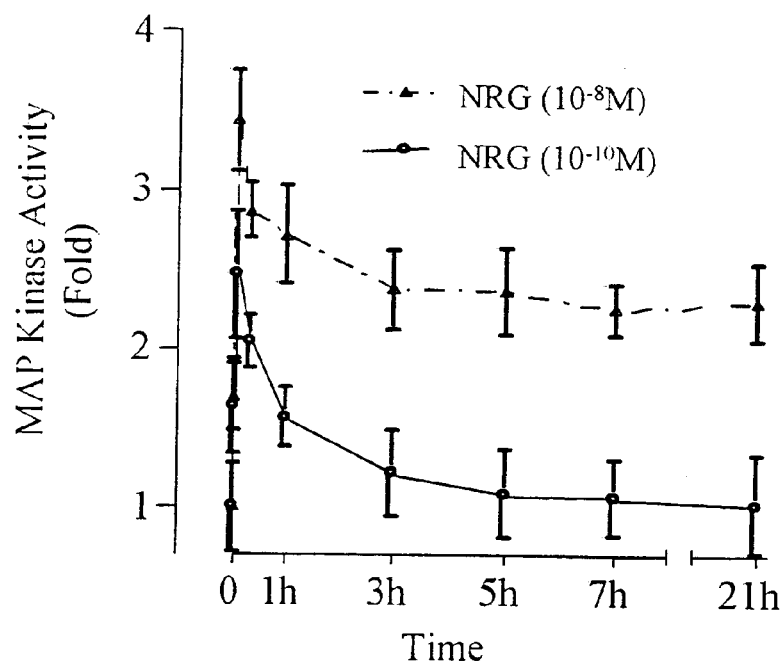
Figure 3C:
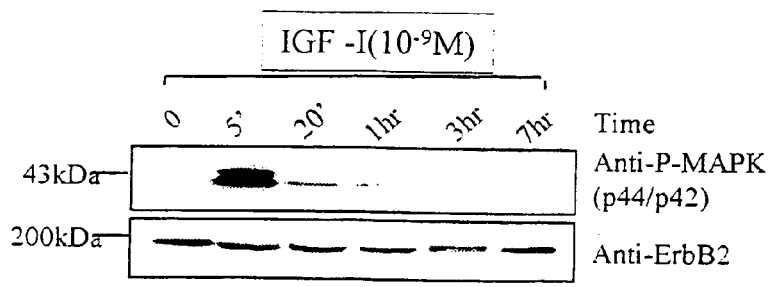

Activation of the ErbB receptor family initiates a cascade of molecular interactions, ultimately resulting in the stimulation of MAP kinases. The duration of MAP kinase activation is critical for cell-fate decisions. Therefore, the present inventor investigated the time course of MAP kinase phosphorylation after either $10^{-8}$M or $10^{-10}$M rhNRGβ2 treatment, using a specific-phospho-MAP kinase antibody, which recognises phosphorylated p42/p44 MAP kinases. As shown in FIG. 3a, phosphorylation of p42/p44 MAP kinases was sustained for at least 21 hours with the higher dose of rhNRGβ2. MAP kinase activation was transient at the lower ligand concentration, and fell to the basal level in less than three hours. As shown in FIG. 3b, MAP kinase catalytic activity paralleled these changes in phosphorylation. Thus, MAP kinase activity was sustained for at least 21 hours in cells stimulated with $10^{-8}$M rhNRGβ2, but was only transient in cells treated with $10^{-10}$M rhNRGβ2. In contrast to these NRG responses, MAP kinase phosphorylation was transient both with low ($10^{-9}$M) (FIG. 3c) and with high concentrations ($10^{-8}$M or $10^{-7}$M) of IGF-I.

Effect of NRG on IGF-I-Stimulated Myocardial Cell Proliferation

Figure 4A:
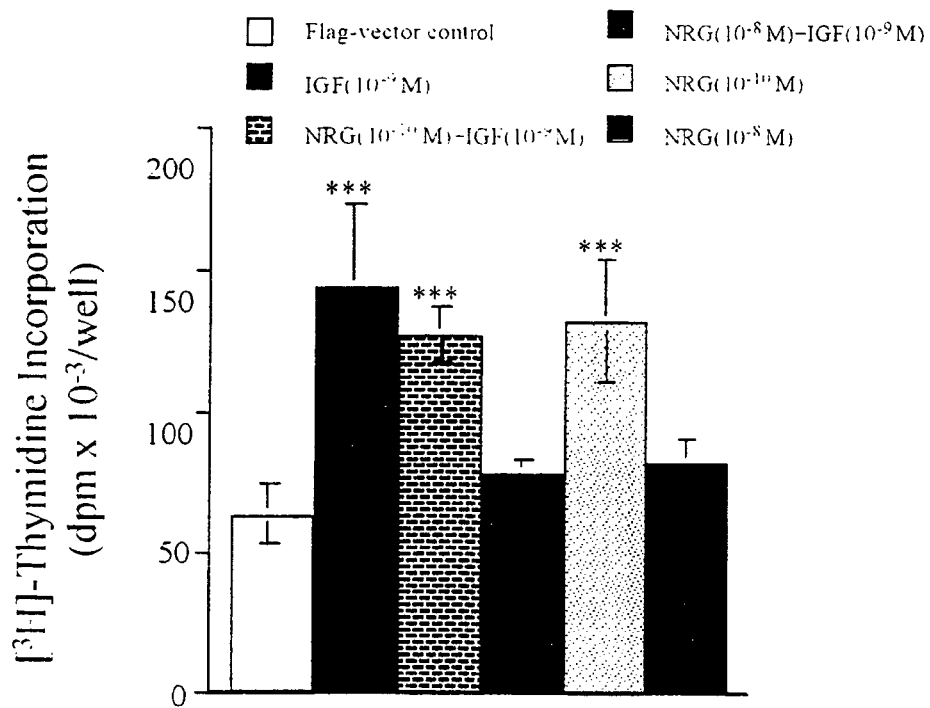
FIG. 4. Effects of NRG on IGF-I stimulated DNA synthesis and MAP kinase phosphorylation. (a) DNA synthesis ([$^3$H] thymidine incorporation) was examined in cultured cells stimulated with a maximal concentration of IGF-I ($10^{-9}$M) in the absence or presence of rhNRGβ2 at concentrations of either $10^{-10}$M or $10^{-8}$M for 20 hrs. Bars show the mean values of data from five samples±1S.E (error bars). Similar results were obtained from three independent experiments. Significant difference (***, $P<0.001$) from the control are indicated. (b) Time course of MAPK phosphorylation in embryonic cardiac muscle cells in response to a mixture of $10^{-9}$M IGF-I and $10^{-8}$M rhNRGβ2 was determined by immunoblotting using a specific anti-phospho-MAPK antibody. ErbB2 expression was evaluated simultaneously to control for protein loading.
Figure 4B:
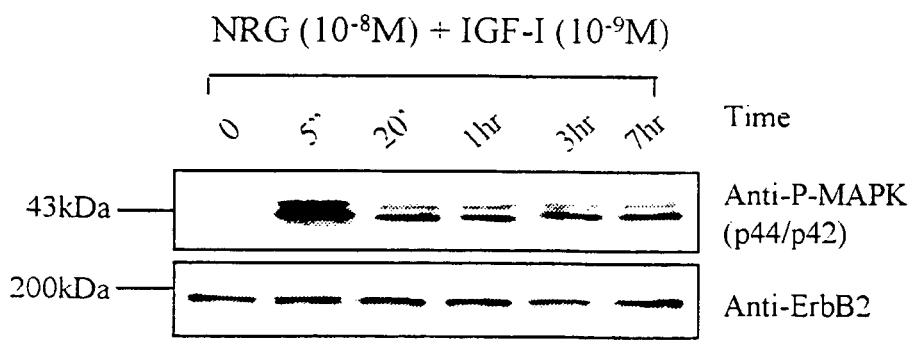

Since myocardial cells are exposed to multiple peptide hormones and growth factors in vivo, the present inventor investigated if the growth inhibitory effects of a high concentration of NRG could oppose the proliferative response of other growth factors. This was achieved by evaluating the effects of both rhNRGβ2 and IGF-I on cardiac myocyte DNA synthesis. As shown in FIG. 4a, a $10^{-10}$M concentration of NRG had little effect on IGF-I ($10^{-9}$M)-stimulated DNA synthesis. However, the $10^{-8}$M concentration significantly blocked the IGF-I response. This indicated that a specific intracellular pathway was activated by the higher concentration of NRG. Interestingly, no additive effect was observed when both IGF-I and the lower concentration of NRG were applied to cells, indicating that the $10^{-9}$M concentration of IGF-I may already be maximal. That the pathway(s) activated by the higher concentration of NRG may be dominant over that activated by IGF-I was further supported by the observation that the combination of IGF-I ($10^{-9}$M) and rhNRGβ2 ($10^{-8}$M) resulted in sustained MAP kinase phosphorylation (compare FIG. 4b and FIG. 3c)

NRG and $p21^{CIP1}$ Expression

Figure 5A:
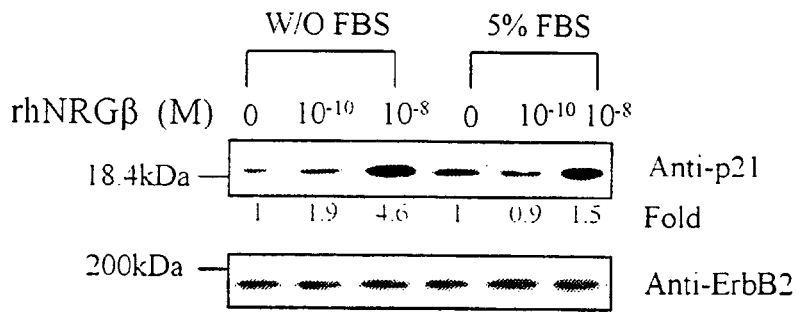
FIG. 5. NRG-mediated induction of $p21^{CIP1}$ expression. (a) $p21^{CIP1}$ expression in cultured cardiac muscle cells stimulated either with $10^{-10}$M or $10^{-8}$M rhNRGβ2 in the absence or presence of serum (5% of FBS) for 24 hrs; or (b) with $10^{-10}$M or $10^{-8}$M IGF-I. After the various treatments, $p21^{CIP1}$ expression was evaluated by immunoblot analysis using an anti-$p21^{CIP1}$ antibody. ErbB2 expression was evaluated simultaneously to control for protein loading. Fold changes in $p21^{CIP1}$ expression, normalised for protein loading, are shown. (c) Effect of the MEK inhibitor (PD98059) (50 µM) on rhNRGβ2 (either at $10^{-10}$M or $10^{-8}$M)-mediated stimulation of $p21^{CIP1}$ expression in cultured embryonic cardiac muscle cells in the absence of serum. $p21^{CIP1}$ was detected by immunoblot analysis using an anti-$p21^{CIP1}$ antibody. Fold changes in $p21^{CIP1}$ expression, normalised for protein loading, are shown. (d) Effects of PD98059 on the inhibition of NRG- or IGF-I-activated MAP kinase activities were monitored by a measurement of p42/44 MAP kinase phosphorylation after cells were stimulated with NRG or IGF-I for 5 min. p42/44 MAP kinase phosphorylation was evaluated by immunoblot analysis using anti-phospho-p42/44 or anti-p42/44 MAP kinase antibodies. The same amount of whole cell extract (20 µg protein) was loaded, and normalised for p42/44 MAP kinase expression, using an anti-p42/44 MAP kinase antibody.
Figure 5B:
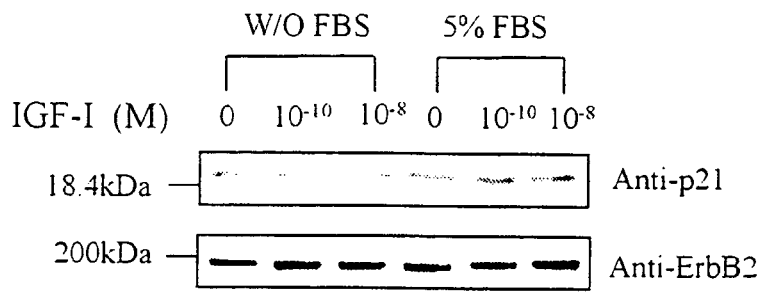
Figure 5C:
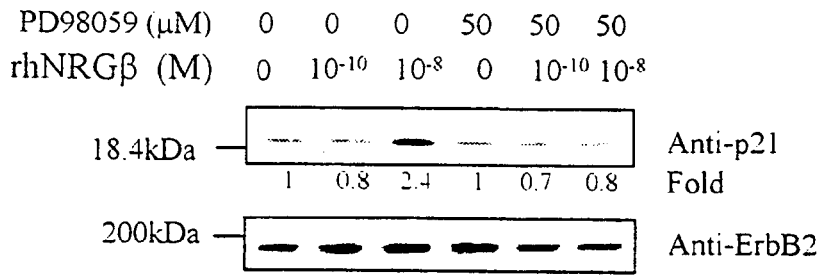
Figure 5D:
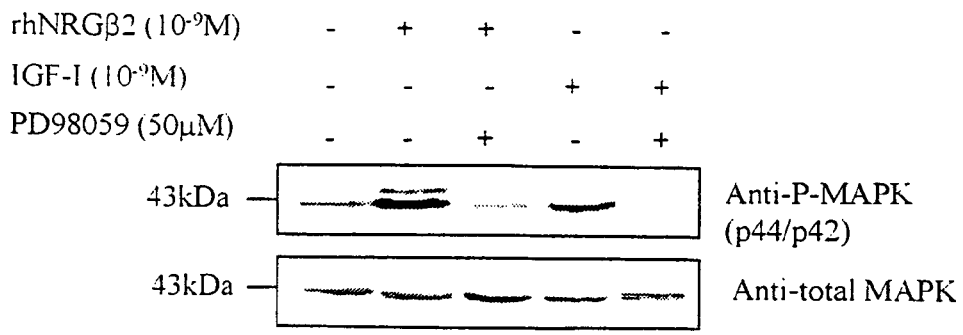

Since sustained activation of MAP kinase is directly related to the expression of $p21^{CIP1}$ in other types of cells,[31] and accumulation of $p21^{CIP1}$ leads to cell cycle arrest at the G1 phase,[32, 33] it was asked if the sustained activation of MAP kinases leads to a higher level of $p21^{CIP1}$ expression in embryonic cardiac muscle cells. As shown in FIG. 5a, an increase in $p21^{CIP1}$ expression was observed only with the higher concentration of rhNRGβ2. This effect on $p21^{CIP1}$ expression was independent of the cell culture conditions used, since similar effects were observed with both serum-free and serum-containing culture medium. Enhanced $p21^{CIP1}$ expression with $10^{-8}$M rhNRGβ2 was sustained for at least 24 hours (a 48 hour incubation of cells with rhNRGβ2 results in an identical expression of $p21^{CIP1}$), and thus, may be critical for the inhibition of DNA synthesis in cardiac muscle cells treated with the high concentration of NRG. As shown in FIG. 5b, IGF-I did not stimulate $p21^{CIP1}$ expression. To evaluate if the $p21^{CIP1}$ response involves MAP kinase activation, cardiomyocytes were treated with the specific MAP kinase kinase (MEK1) inhibitor (PD98059). Both in the presence or absence of serum, PD98059 blocked the increase in $p21^{CIP1}$ expression induced by $10^{-8}$M rhNRGβ2 (FIG. 5c), as well as the increase in p42/44 MAP kinase phosphorylation (FIG. 5d).

NRG Sarcomeric Structure and MHC Expression

Figure 6A:
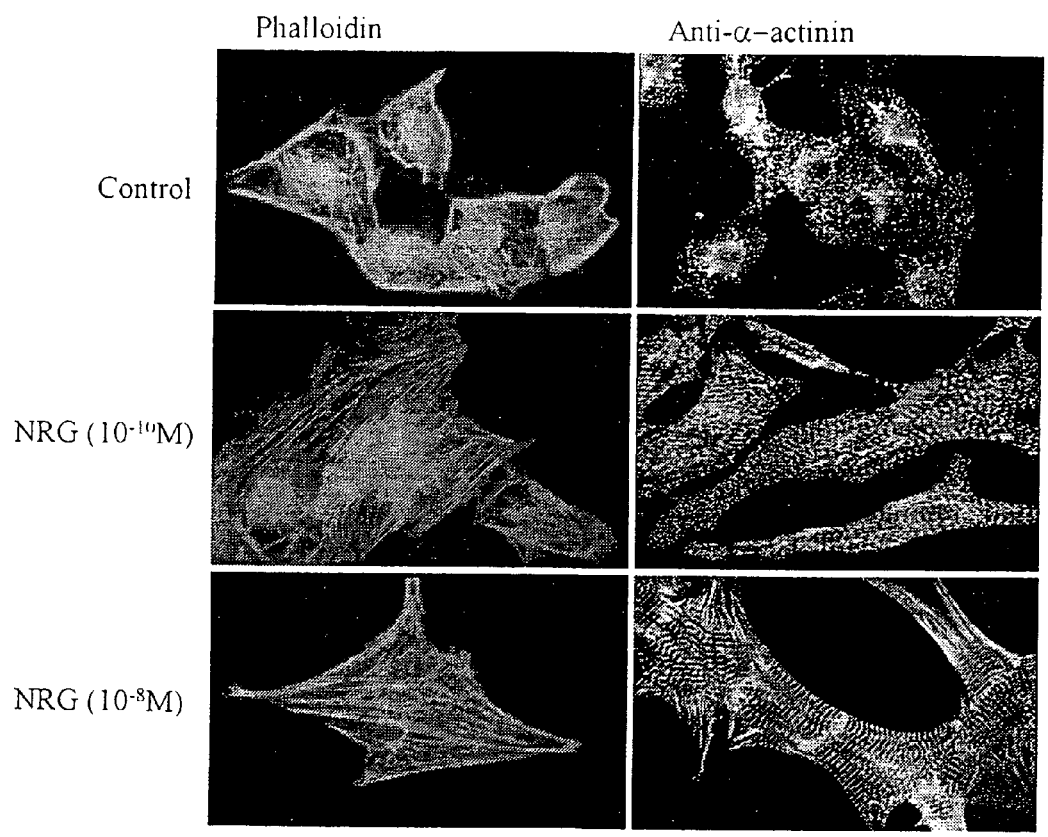
FIG. 6. Effects of NRG on cardiac sarcomere assembly and myosin heavy chains expression. (a) E12.5 mouse cardiac muscle cells were cultured in serum-free medium (control) or stimulated with $10^{-10}$ or $10^{-8}$ M rhNRGβ2 (NRG) for 48 hrs. Cells were then stained with phalloidin (left panels) or evaluated for anti-α-actinin immunoflorescency (right panels). (b) Sarcomeric myosin heavy chain and α-actin expression in rhNRGβ2-stimulated embryonic mouse cardiac muscle cells were evaluated by immunoblot analysis using an anti-sarcomeric myosin heavy chain antibody (MF20) or an anti-α-actin antibody. The same amount of whole cell extracts (20 µg proteins) was loaded into each lane for SDS-PAGE fractionation.
Figure 6B:
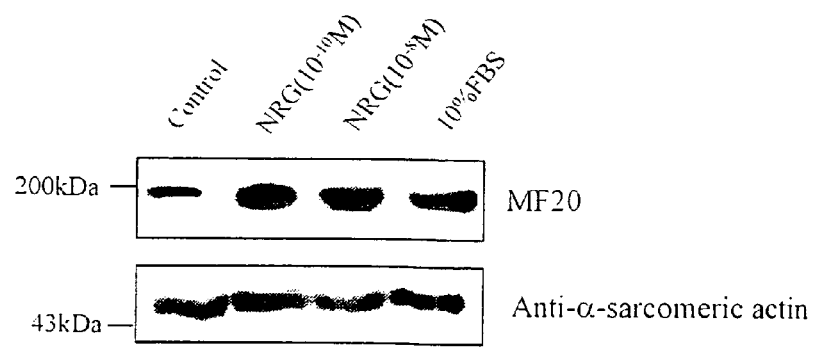

To examine if NRG also affects embryonic myocardial cell structure and function, the effects of NRG on cardiomyocyte cytoskeletal and sarcomeric structures were evaluated. As shown in FIG. 6a, rhNRGβ2 ($10^{-8}$M) stimulated both sarcomeric actin reorganisation (phalloidin staining) and cardiac contractile unit assembly (staining of α-actinin in Z-bands). In contrast, effects of $10^{-10}$M rhNRGβ2 were much less evident (FIG. 6a). A role for NRG in the regulation of myocardial cell function was also evident by the observation that rhNRGβ2 enhanced expression of sarcomeric myosin heavy chains, while sarcomeric actin expression remained unchanged (FIG. 6b). Moreover, the effects of rhNRGβ2 on cardiomyocytes were also sensitive to MEK1 inhibition by PD98059.

Discussion

Evidence provided indicates that ligand (NRG) concentration is a an important factor in determining either the transient or sustained activation states of MAP kinases. The latter results in increased expression level of the Cdk inhibitor, $p21^{CIP1}$, and is associated with decreased DNA synthesis in embryonic myocardial cells. This finding provides clear support that the ligand gradient may decide cell fate in cell differentiation and embryo development, and further furnishes molecular insights on how intracellular signalling pathways distinguish the signal strength based on ligand concentrations.

The importance of ligand concentration in cell differentiation has been suspected for some time based on the following observations:

i) embryo developmental patterning is associated with a ligand gradient;
ii) ligand concentration is critical for cell differentiation in vitro, and
iii) overexpression of receptors in cells changes their fate in response to ligand stimulation.

Taking these observations into consideration, NRG concentration-dependent MAP kinase activation in embryonic myocardial cells establishes a model for further delineating the mechanisms of erbB receptor-coupled cell signalling in reaction to changes in ligand concentration.

The notion that NRG is a myocardial cell differentiation factor is supported by the finding that NRG induces expression of $p21^{CIP1}$ in embryonic myocardial cells. As $p21^{CIP1}$ is well documented to be an inhibitor of Cdk, which promotes entry from the G1 to the S phase of the cell cycle, increased expression of this protein in myocardial cells could be critical for the initiation of terminal differentiation. This is also supported by previous findings that $p21^{CIP1}$ expression increases in vivo with the onset of myocardial cell terminal differentiation (Parker et al. (1995) Science 267:1024–1027), as well as with skeletal muscle cell differentiation (Dias et al. (1994) Semin. Diagn Pathol. 11:3–14). In the latter process, increased $p21^{CIP1}$ expression eventually results in an exit from the cell cycle and differentiation. Since increase in $p21^{CIP1}$ expression occurs prior to that of other cell cycle regulators, it is used as an early marker for skeletal muscle differentiation. As demonstrated here, expression of $p21^{CIP1}$ is concomitant with the decrease in DNA synthesis in NRG-stimulated myocardial cells, suggesting the physiological role of NRG-stimulated $p21^{CIP1}$ expression in these cells. Furthermore, the inhibition of both MAP kinases and $p21^{CIP1}$ by the ERK kinases inhibitor assessed that NRG-stimulated $p21^{CIP1}$ expression is a direct result of activation of MAP kinases.

The sustained activation of MAP kinases is required for induction of $p21^{CIP1}$ constitutive expression in cultured myocardial cells, whereas transient MAP kinase activation results in temporal expression of $p21^{CIP1}$. The latter is presumably insufficient to regulate the Cdk activity, since $p21^{CIP1}$ will be quickly degraded and constitutive expression is essential for blocking the cyclin/Cdk complex. In PC12 cells, sustained activation of the MAP kinase pathway is confined to a response to specific signals from NGF receptors. The sustained activation of MAP kinases causes PC12 cell differentiation becoming neuronal cells. This pathway in cardiac myocytes, however, is able to differentially respond to NRG concentration-based signal strength.

Further evidence support that NRG is a differentiation factor is that NRG stimulate assembly of sarcomeric and cytoskeleton structures, which occur as myocardial progenitor cells differentiate to cardiac muscle cells. Previous observation also indicated that more differentiated cells have more organised sarcomeres (Rumynatsev, P.P. (1977) in International Review Cytology 51, pp 187–273). In a comparison of cells stimulated with either PE or IGF-1, NRG-stimulated cells have the best organised sarcomeres. More importantly, when NRG is mixed with PE or IGF-1, NRG greatly improved sarcomeres, indicating that NRG is dominant in stimulation of sarcomere assembly in presence of other cell signals. NRG overrides the PE-mediated negative regulation of MHC-a expression, indicating that NRG is involved in the maintenance of adult type of contractile proteins. As previous studies indicated that NRG, ErbB2 and ErbB4 are expressed in adult heart, NRG should play a role in the maintenance of myocardial cell differentiation state.

Two very important features of heart failure associated with cardiomyopathy in patients are disarrays of myofibers and sarcomeres. The former is the loose of the cell-cell adhesion and the latter is the loose of the sarcomere organisation. These pathological conditions widely exist from congestive heart failure to dilated cardiomyopathy and severely affect heart function. Currently no treatment is target on the assembly of cell-cell adhesion and sacomere structures. NRG clearly plays a role in the process of the assembly and maintenance of cell-cell adhesion and sarcomeric structures. That NRG stimulates myocardial cell differentiation and the assembly of sarcomeric structures indicates that cardiac muscle cell differentiation is associated with its cell structure remodelling. Such a conclusion is consistent with general observation from heart muscle cell differentiation during heart development: differentiated muscle cells always contain well organised sarcomeres.

In summary, that NRG is a differentiation factor for myocardial cells is supported by following evidence:

i) NRG stimulates sustained activation of MAP kinases;
ii) NRG enhances $p21^{CIP1}$ expression;
ii) NRG inhibits IGF-1-stimulated DNA synthesis; and
iv) NRG stimulates the myocardial cell assembly of sarcomeric and cytoskeleton structures.
v) NRG stimulates expression of the adult-type MHC gene.

Therapeutic Use

The present invention provides methods for treating or preventing heart failure or cardiac muscle cell hypertrophy in a mammal by providing an effective amount of a neuregulin. Preferably, the mammal is a human patient suffering from or at risk of developing heart failure.

The present invention is useful in preventing heart failure and cardiomyopathy in patients being treated with a drug which cause cardiac hypertrophy or congestive heart failure, e.g., fludrocortisone acetate or herceptin. In the method of the invention, a neuregulin polypeptide can be given prior to, simultaneously with, or subsequent to a drug which causes cardiac diseases.

In the therapeutic method of the invention, a neuregulin polypeptide is administered to a human patient chronically or acutely, for example by injection into the patient's vein. Optionally, neuregulin is administered chronically in combination with an effective amount of a compound that acts to suppress a different hypertrophy induction pathway than a neuregulin Additional optional components include a cardiotrophic inhibitor such as a Ct-1 antagonist, an ACE inhibitor, such as captopril, and/or human growth hormone and/or IGF-I in the case of congestive heart failure, or with another anti-hypertrophic, myocardiotrophic factor, anti-arrhythmic, or inotropic factor in the case of other types of heart failure or cardiac disorder.

The present invention can be combined with current therapeutic approaches for treatment of heart failure, e.g., with ACE inhibitor treatment. ACE inhibitors are angiotensin-converting enzyme inhibiting drugs which prevent the conversion of angiotensin I to angiotensin II. The ACE inhibitors may be beneficial in congestive heart failure by reducing systemic vascular resistance and relieving circulatory congestion. ACE inhibitors include drugs designated by the trademarks Accupril® (quinapril), Altace® (ramipril), Capoten® (captopril), Lotensin® (benazepril), Monopril® (fosinopril), Prinivil® (lisinopril), Vasotec® (enalapril), and Zestril® (lisinopril).

The present invention can be combined with the administration of drug therapies for the treatment of heart diseases such as hypertension. For example, a neuregulin polypeptide can be administered with endothelin receptor antagonists, for example, and antibody to the endothelin receptor, and peptide or other such small molecule antagonists; O-adrenoreceptor antagonists such as carvedilol; $\alpha_1$-adrenoreceptor antagonists; anti-oxidants; compounds having multiple activities (e.g., $\beta$-blocker/$\alpha$-blocker/anti-oxidant); carvedilol-like compounds or combinations of compounds providing multiple functions found in carvedilol; growth hormone, etc.

Neuregulin agonists alone or in combination with other hypertrophy suppressor pathway agonists or with molecules that antagonise known hypertrophy induction pathways, are useful as drugs for in vivo treatment of mammals experiencing heart failure, so as to prevent or lessen heart failure effects.

Therapeutic formulations of agonist(s) for treating heart disorders are prepared for storage by mixing the agonist(s) having the desired degree of purity with optional physiologically acceptable carriers, excipients, or stabilisers (*Remington's Pharmaceutical Sciences*, 16$^{th}$ edition, Oslo, A., Ed., 1980), in the form of lyophilised cake or aqueous solutions. Acceptable carriers, excipients, or stabilisers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or non-ionic surfactants such as Tween, Pluronics, or polyethylene glycol (PEG). The antagonist(s) are also suitably linked to one of a variety of nonproteinaceous polymers, e.g., polyethylene glycol, polypropylene glycol, or polyalkylenes, in the manner set forth in U.S. Pat. Nos. 4,640,835; 4,496,689; 4,301,144; 4,670,417; 4,791,192 or 4,179,337. The amount of carrier used in a formulation may range from about 1 to 99%, preferably from about 80 to 99%, optimally between 90 and 99% by weight.

The agonist(s) to be used for in vivo administration should be sterile. This is readily accomplished by methods known in the art, for example, by filtration through sterile filtration membranes, prior to or following lyophilisation and reconstitution. The agonist(s) ordinarily will be stored in lyophilised form or in solution.

Therapeutic agonist compositions generally are placed into a container having a sterile access port, for example, an intravenous solution bag or vial having a stopper pierceable by a hypodermic injection needle. The agonist(s) administration is in a chronic fashion only, for example, one of the following routes: injection or infusion by intravenous, intraperitoneal, intracerebral, intramuscular, intraocular, intraarterial, or intralesional routes, orally or using sustained-release systems as noted below. Agonist(s) are administered continuously by infusion or by periodic bolus injection if the clearance rate is sufficiently slow, or by administration into the blood stream or lymph. The preferred administration mode is targeted to the heart, so as to direct the molecule to the source and minimise side-effects of the agonists.

Suitable examples of sustained-release preparations include semipermeable matrices of solid hydrophobic polymers containing the protein, which matrices are in form of shaped articles, e.g., films, or microcapsules. Examples of sustained-release matrices include polyesters, hydrogels (e.g., poly(2-hydroxyethyl-methacrylate) as described by Langer et al. (1981) J. Biomed. Mater. Res. 15: 167–277 and Langer (1982) Chem. Tech. 12: 98–105, or poly(vinyl alcohol)), polylactides (U.S. Pat. No. 3,773,919, EP 58,481), copolymers of L-glutamic acid and gamma ethyl-L-glutamate (Sidman et al. (1983) Biopolymers 22: 547–556), non-degradable ethylene-vinyl acetate (Langer et al. (1981) supra) degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133, 988).

The agonist(s) also may be entrapped in microcapsules prepared, for example, by coacervation techniques or by interfacial polymerisation (for example, hydroxymethylcellulose or gelatin-microcapsules and poly-[methylmethacylate] microcapsules, respectively, in colloidal drug delivery systems (for example, liposomes, albumin microspheres, microemulsions, nano-particles and nanocapsules), or in macroemulsions. Such techniques are disclosed in *Remington's Pharmaceutical Sciences*, supra.

While polymers such as ethylene-vinyl acetate and lactic acid-glycolic acid enable release of molecules for over 100 days, certain hydrogels release molecules for shorter time periods. When encapsulated molecules remain in the body for a long time, they may denature or aggregate as a result of exposure to moisture at 37° C., resulting in a loss of biological activity and possible changes in immunogenicity. Rational strategies can be devised for stabilisation depending on the mechanism involved, e.g., using appropriate additives, and developing specific polymer matrix compositions.

Sustained-release agonist(s) compositions also include liposomally entrapped agonists(s). Liposomes containing agonists(s) are prepared by methods known per se: DE 3.218,121; Epstein et al. (1985) Proc. Natl. Acad. Sci. USA 82: 3688–3692; Hwang et al. (1980) Proc. Natl. Acad. Sci. USA 77: 4030–4034; EP 52.322: EP 36,676; EP 88,046; EP 143,949; EP 142,641; Japanese patent application 83–118008; U.S. Pat. Nos. 4,485,045 and 4,544.545; and EP 102, 324. Ordinarily the liposomes are of the small (about 200–800 Å) unilamellar type in which the lipid content is greater than about 30 mol % cholesterol, the selected proportion being adjusted for the optimal agonist therapy. A specific example of suitable sustained-release formulation is in EP 647,449.

An effective amount of NRG to be employed therapeutically will depend, for example, upon the therapeutic objectives, the route of administration, and the condition of the patient Accordingly, it will usually be necessary for the clinician to titre the dosage and modify the route of administration as required to obtain the optimal therapeutic effect.

NRG optionally is combined with or administered in concert with other agents for treating congestive heart failure, including ACE inhibitors, CT-1 inhibitors, human growth hormone, and/or IGF-I. The effective amounts of such agents, if employed, will be at the clinician's discretion. Dosage administration and adjustment are determined by methods known to those skilled in the art to achieve the best management of congestive heart failure and ideally takes into account use of diuretics or digitalis, and conditions such as hypotension and renal impairment. The dose will additionally depend on such factors as the type of drug used and the specific patient being treated. Typically the amount employed will be the same dose as that used if the drug were to be administered without agonist; however, lower doses may be employed depending on such factors as the presence of side-effects, the condition being treated, the type of patient, and the type of agonists and drug, provided the total amount of agents provides an effective dose for the condition being treated.

Thus, for example, in the case of ACE inhibitors, a test dose of enalapril is 5 mg, which is then increased up to 10–20 mg per day, once a day, as the patient tolerates it. As another example, captopril is initially administered orally to human patients in a test dose of 6.25 mg and the dose is then escalated, as the patient tolerates it to 25 mg twice per day (BID) or three times per day (TID) and may be titrated to 50 mg BID or TID. Tolerance level is estimated by determining whether decrease in blood pressure is accompanied by signs of hypotension. If indicated, the dose may be increased up to 100 mg BID or TID. Captopril is produced for administration as the active ingredient, in combination with hydrochlorothiazide, and as a pH stabilised core having an enteric or delayed release coating which protects captopril until it reaches the colon. Captopril is available for administration in tablet or capsule form. A discussion of the dosage. Administration, indications and contraindications associated with captopril and other ACE inhibitors can be found in the Physicians Desk Reference, Medical Economics Data Production Co., Montvale, NJ. 2314–2320 (1994).

In an example of an injectable therapeutic composition of neuregulin, the formulation contains 1% neuregulin and 99% saline, where neuregulin is a polypeptide thereof. In another example of an injectable therapeutic composition of neuregulin, the formulation contains 5% of the neuregulin polypeptide, 1% ACE inhibitor captopril, and 94% saline.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of inducing remodeling of cardiac muscle cell sarcomeric and cytoskeleton structures or cell-cell adhesions, which method comprises contacting cardiac muscle cells with a neuregulin protein consisting of the amino acid sequence set forth in SEQ ID NO:2, in the amount sufficient to activate the MAP kinase pathway in said cardiac muscle cells and induce remodeling of said cardiac muscle cell sarcomeric and cytoskeleton structures or cell-cell adhesions.

2. The method of claim 1, wherein the neuregulin protein is used in an amount that is at least $10^{-8}$M.

3. The method of claim 1, wherein the cardiomyocyte or the cardiac muscle cells exist in a mammal.

4. The method of claim 3, wherein the mammal is a human.

5. The method of claim 4, wherein the human has or is suspected of having a heart failure.

6. The method of claim 5, wherein the heart failure is a disease state selected from the group consisting of congestive heart failure, myocardial infarction, tachyarrhythmia, familial hypertrophic cardiomyopathy, ischaemic heart disease, idiopathic dilated cardiomyopathy and myocarditis.

7. The method of claim 5, wherein the heart failure is in the form of ischaemic, congenital, rheumatic, or idiopathic.

8. The method of claim 5, wherein the heart failure results from disassociation of cardiac muscle cell-cell adhesion and/or the disarray of sarcomeric structures in the mammal.

9. The method of claim 3, wherein the neuregulin protein is administered with a pharmaceutically acceptable carrier or excipient.

10. The method of claim 1, wherein the contact of the cardiac muscle cells with the neuregulin protein decreases DNA synthesis in the cardiac muscle cells.

11. The method of claim 1, wherein the contact of the cardiac muscle cells with the neuregulin protein results in sustained activation of the MAP kinase pathway in the cardiac muscle cells.

12. The method of claim 3, wherein the neuregulin protein is administered orally, using a sustained-release system or via injection or infusion.

13. The method of claim 12, wherein the injection or infusion is selected from the group consisting of intravenous, intraperitoneal, intracerebral, intramuscular, intraocular, intraarterial and intralesional injection or infusion.

14. The method of claim 1, which further comprises contacting the cardiac muscle cells with an effective amount of an agent which causes cardiac hypertrophy or congestive heart failure.

15. The method of claim 14, wherein the agent which causes cardiac hypertrophy or congestive heart failure is fludrocortisone acetate or herceptin.

16. The method of claim 1, which further comprises contacting the cardiac muscle cells with an effective amount of an agent that acts to suppress a hypertrophy induction pathway different from the pathway suppressed by the neuregulin.

17. The method of claim 16, wherein the agent that acts to suppress a hypertrophy induction pathway different from the pathway suppressed by the neuregulin is selected from the group consisting of a cardiotrophic inhibitor, an angiotensin-converting enzyme (ACE) inhibitor, a human growth hormone, an IGF-I, an anti-hypertrophic, myocardiotrophic factor, an anti-arrhythmic factor and an inotropic factor.

18. The method of claim 1, which further comprises contacting the cardiac muscle cells with an effective amount of an angiotensin-converting enzyme (ACE) inhibitor.

19. The method of claim 18, wherein the ACE inhibitor is selected from the group consisting of quinapril, ramipril, captopril, benazepril, fosinopril, lisinopril, enalapril and lisinopril.

20. The method of claim 1, which further comprises contacting the cardiac muscle cells with an effective amount of an agent for treating hypertension.

21. The method of claim 20, wherein the agent for treating hypertension is selected from the group consisting of an antibody to the endothelin receptor, a β-adrenoreceptor antagonist, an $α_1$-noreceptor antagonist, an anti-oxidant, a β-blocker and a growth hormone.

22. A method for treating or delaying disassociation of cardiac muscle cell-cell adhesion and/or the disarray of sarcomeric structures in a mammal, which method comprises administering to a mammal, to which such treatment or delay is needed or desirable, a neuregulin protein consisting of the amino acid sequence set forth in SEQ ID NO:2, in an amount sufficient to activate the MAP kinase pathway in said mammal, whereby said disassociation of cardiac muscle cell-cell adhesion and/or the disarray of sarcomeric structures is treated or delayed in said mammal.

23. The method of claim 22, wherein the mammal is a human.

24. The method of claim 23, wherein the human has or is suspected of having a heart failure.

25. The method of claim 24, wherein the heart failure is a disease state selected from the group consisting of congestive heart failure, myocardial infarction, tachyarrhythmia, familial hypertrophic cardiomyopathy, ischaemic heart disease, idiopathic dilated cardiomyopathy and myocarditis.

26. The method of claim 24, wherein the heart failure is in the form of ischaemic, congenital, rheumatic, or idiopathic.

27. The method of claim 22, wherein administration of the neuregulin protein decreases DNA synthesis in the cardiac muscle cells of the mammal.

28. The method of claim 22, wherein administration of the neuregulin protein results in sustained activation of the MAP kinase pathway in the cardiac muscle cells of the mammal.

\* \* \* \* \*

```
                      SEQUENCE LISTING

<160> NUMBER OF SEQ ID NOS: 2

<210> SEQ ID NO 1
<211> LENGTH: 114
<212> TYPE: DNA
<213> ORGANISM: Homo sapiens

<400> SEQUENCE: 1
agccatcttg taaatgtgcg gagaaggaga aaactttctg tgtgaatgga ggggagtgct      60
tcatggtgaa agacctttca aacccctcga gatacttgtg aggagctgta ccag          114

<210> SEQ ID NO 2
<211> LENGTH: 61
<212> TYPE: PRT
<213> ORGANISM: Homo sapiens

<400> SEQUENCE: 2

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60
```